United States Patent [19]
Cho et al.

[11] Patent Number: 4,910,404
[45] Date of Patent: Mar. 20, 1990

[54] CT COMPUTED TOMOGRAPH

[75] Inventors: Yoshio Cho, Hyogo; Masahiko Kanda, Osaka, both of Japan

[73] Assignee: Sumitomo Electric Industries, Ltd., Osaka, Japan

[21] Appl. No.: 311,658

[22] Filed: Feb. 16, 1989

[30] Foreign Application Priority Data

Feb. 17, 1988 [JP] Japan .................. 63-36203

[51] Int. Cl.⁴ .............................................. A61B 5/00
[52] U.S. Cl. .................................. 250/358.1; 250/341; 250/350; 128/633
[58] Field of Search .................. 250/358.1, 341, 350, 250/349; 128/633, 664

[56] References Cited

U.S. PATENT DOCUMENTS 4,281,645 8/1981 Jöbsis .................................. 128/633

FOREIGN PATENT DOCUMENTS 115232 7/1982 Japan .
72542 4/1985 Japan .

OTHER PUBLICATIONS

"Optical Diffusion in Blood" by C. C. Johnson, IEE Transaction on Bio-Medical Engineering, vol. BME-17, No. 2, 1970, pp. 129-133.

Primary Examiner—Carolyn E. Fields
Attorney, Agent, or Firm—W. G. Fasse; D. H. Kane, Jr.

[57] ABSTRACT

A CT computed tomograph comprises a scanner (51) which surrounds a living body of a person to be examined. Ultrashort light pulses of the $i$th wavelength are applied to the living body from a sample light transmitting path (80k) corresponding to the $k$th cell of this scanner and the sample light pulses received by a sample light receiving path (81l) corresponding to the $l$th cell and reference light pulses transmitted from a reference light path (79) and a delay light path (78) are converged by a converging lens (75). A CPU(64) counts photons outputted from a photomultiplier (22) based on the converged light pulses and calculates an average value by averaging a predetermined number of count values. A delay amount of the reference light pulses through the delay light path (78) is changed based on the average value and, based on delay time and an average value in the delay time, a photon count value $S_{0i}(k, l)$ obtained by counting the photons of the second harmonic when the delay amount of the reference light pulses is a predetermined value is stored. Based on the photon average value $S_{0i}(k, l)$, a tomographic image of the metabolism of the living body is evaluated.

7 Claims, 6 Drawing Sheets

FIG.1
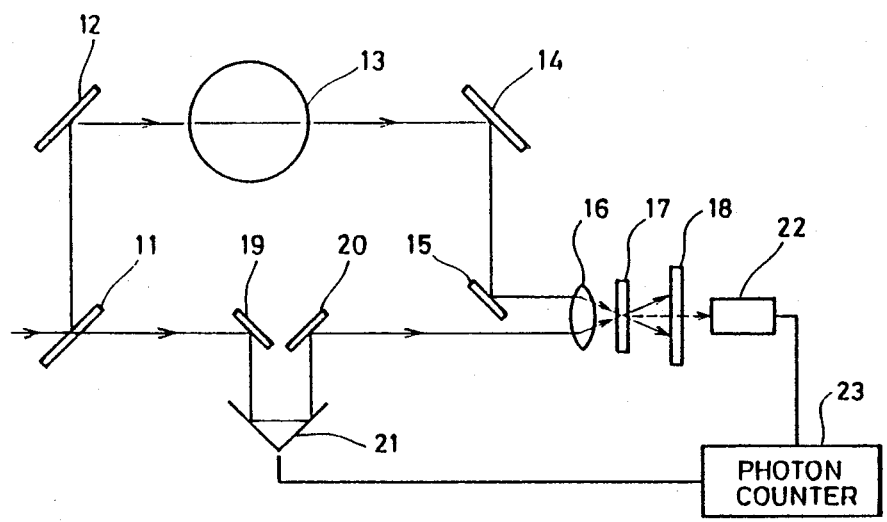
FIG.2
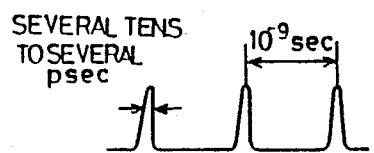
FIG.3a REFERENCE LIGHT PULSE
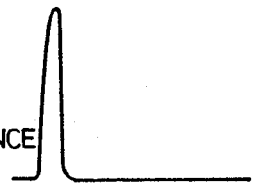
FIG.3b SAMPLE LIGHT PULSE
FIG.4
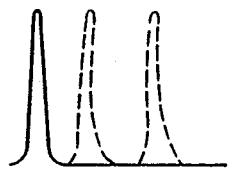
FIG.3c S(t)

FIG. 5a ULTRASHORT LIGHT PULSES 
FIG. 5b PHOTON COUNT INTERVAL 
FIG. 5c PHOTON COUNT OUTPUT OF S 
FIG. 5d SAMPLE-AND-HOLD SIGNAL 
FIG. 5e OUTPUT OF SAMPLING 
FIG. 5f OUTPUT OF SAMPLING-AND-HOLDING 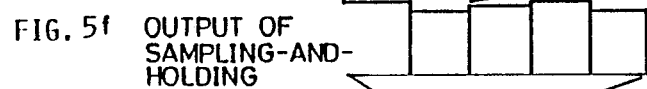
FIG. 5g S(t) 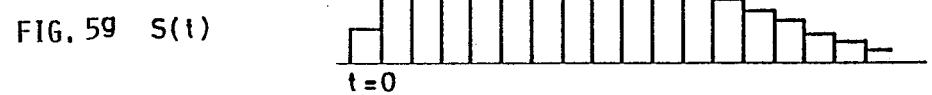
t=0

CT COMPUTED TOMOGRAPH

BACKGROUND OF THE INVENTION

1. Field of the Invention

The present invention relates to a CT computed tomograph, namely, an apparatus of tomography using rays and particularly to a CT computed tomograph which measures, in an non-invasive manner, changes in an oxidation-reduction action of cytoplasmic cytochrome as well as changes in an oxygenated state of hemoglobin and a blood quantity in an organ or other part of a human body or an animal body.

2. Description of the Background Art

FIG. 11 is a diagram showing a construction of a conventional apparatus for measuring metabolism in an organ of a body. FIGS. 12 and 13 are diagrams showing light paths detected in the conventional measuring apparatus.

The apparatus shown in FIG. 11 is described in Japanese Patent Laying-Open No. 115232/1982. In this example of FIG. 11, a near infrared radiation source 1 emits near infrared rays of different wavelengths alternately. The near infrared rays pass through the head 3 of a human body through an optical fiber 2 so that a detection system 4 measures the intensity of the rays. An adjuster 5 adjusts the speed and the order of monochromatic flashes and demodulates the detected light signal. A feedback adjusting system 6 maintains the light signal detected by one wavelength to be constant by negative electricity feedback adjustment of the detection sensitivity and corrects a change in the transmittivity caused by the change in the blood quantity of the examined organ during the transmission time. An output adjusting circuit 7 outputs a feedback voltage blood quantity indicating signal simultaneously with received reference and measurement signals.

In the above mentioned apparatus shown in FIG. 11, a beam of 700 nm to 1300 nm is applied to the head 3 and changes in the oxygenated state of hemoglobin in the brain, the quantity of blood and the oxidation-reduction action of cytoplasmic cytochrome are detected by detection of the light transmitted through the head 3. This detection makes use of the characteristics that there is a small peak at about 760 nm of deoxygenated hemoglbin using an isosbestic point 805 nm of hemoglobin as a reference wavelength and that there is an oxygen-dependent absorbant of cytochrome aa3 in the wavelength range from 700 nm to 1300 nm.

In addition, Japanese Patent Laying-Open No. 72542/1985 proposes a tissue metabolism measuring apparatus which makes it possible to observe quantitatively in a two-dimentional distribution the state of binding of protein with oxygen molecules such as hemoglobin or myoglobin in a living body and to observe in a two-dimensional distributin the oxygen density of cytocondolia based on the oxidized and reduced state of cytochrome groups as a constituent of a respiratory chain.

However, if light of 700 nm to 1300 nm having a higher transmittivity through the living body than a visible radiation range is applied to the living body and the light transmitted therethrough is detected, the incident light has a short wavelength compared with the size of hemoglobin. Consequently, the incident light is diffused and absorbed immediately after the incidence and the detected light catches the component of the diffused light.

Those characteristics are described for example in "Optical Diffusion in Blood" by C. C. Johnson, IEEE TRANSACTION ON BIO-MEDICAL ENGINEERING, Vol. BEM-17 No. 2, 1970, pp. 129-133.

More specifically, as shown in FIG. 12, if a detector 9 is adapted to detect light applied to the living body, the light detected by the detector 9 includes not only the light transmitted through a light path 10a connecting the incident light and the detector 9 as a straight line but also the light diffused and transmitted to the other light paths 10b and 10c than the light path 10a. Thus, whenever the transmitted light is detected, the paths through which the detected light passes in the living body cannot be specified and in the case of the apparatus as shown in FIG. 11, it is possible to obtain only information of the whole of the internal of the living body t be measured or information of a light path (shown by the hatched area in FIG. 13) having a considerably larger width than the light path 10a connecting the incident light and the detector 9. In the case of diagnosing clinically an organic disease such as interruption in blood circulation or the degree of such disease, the position of such disease is in question and the information of such a wide range of the internal of the giving body is useless.

SUMMARY OF THE INVENTION

Therefore, a principal object of the present invention is to provide a CT computed tomograph which makes it possible to observe tissue metabolssm such as blood circulation or respiration at an accurate position by detecting only light of straight line component which connects incident light to a detecting portion.

Briefly stated, the present invention is constructed in the following manner. High-repetitive ultrashort light pulses of a plurality of wavelengths are generated from a light source and those ultrashort light pulses are branched to reference light pulses and sample light pulses by light branching means so that the branched reference light pulses are introduced into a reference light path. A ring-shaped scanner is provided to surround a living body of a person to be examined. Sample light transmitting paths are provided in a plurality of cells sectioned at predetermined intervals along an inner circumference of the scanner, opposite to the living body and the branched sample light pulses are applied to the living body from the sample light transmitting paths. In each cell of the scanner, a sample light receiving path is provided to oppose to the living body, so that the sample light pulses transmitted through the living body are introduced into light converging means. Light pulses in any one of the light paths out of the reference light path, the sample light transmitting paths and the sample light receiving paths are delayed by a predetermined time by delay means. The reference light pulses and the sample light pulses are collected by the light converging means and based on the collected light pulses, a second harmonic is generated from a crystal and the second harmonic is detected by second harmonic detecting means.

By using evaluation control means, the ultrashort pulses of the ith wavelength are applied to the living body in the scanner from the sample light transmitting path corresponding to the kth cell and the reference light pulses related with the sample light pulses received by the sample light receiving path corresponding to the lth cell are collected by the light converging means. Then, the evaluation control means counts photons outputted from the second harmonic detecting means based on the collected light pulses, calculates an average value by averaging a predetermined number of count values and changes the delay amount of either the sample light pulses or the reference light pulses by the delay means base on the average value. Further, the evaluation control means counts photons of the second harmonic when the delay amount of the reference light pulses and the sample light pulses is a predetermined value, based on the delay time and the average value in the delay time, and stores a photon average value $S_{0i}(k, l$ (where $k, l, 1 = 1, 2, \ldots n$). Thus, the evaluation control means evaluates and outputs a tomographic image of metabolism in the living body based on the photon average value $S_{01}(k, l)$.

Consequently, according to the present invention, evaluation is effected to obtain an average value of counts of photons of the second harmonic generated from the crystal when the delay amount of the sample light pulses transmitted through the living body and the reference light pulses is the predetermined value, whereby diffused components in the light transmitted through the living body can be removed and only the component advancing straight in the body can be detected. Accordingly, more accurate position information can be obtained at the time of detecting information in the living body using the transmitted light. In consequence, it becomes possible to monitor a tomographic image indicating metabolism of the living body on a specified axis in the body. In addition, since the high-repetitive ultrashort pulses are utilized, the senitivity of detection of the transmitted light quantity can be improved considerably and since the sensitivity can be changed simply, the operation efficiency can be improved.

According to a preferred embodiment of the invention, each sample light transmitting path is provided with first shutter means for intercepting sample light pulses supplied from the light branching means and each light receiving path is provided with second shutter means for intercepting the sample light pulses transmitted through the living body. Based on the control of the evaluation control means, either one of the first shutter means is opened or closed by first interception drive means and the second shutter means are opened or closed by second interception drive means. In addition, a filter through which only the second harmonic passes is provided between the crystal and the second harmonic detecting means.

According to another preferred embodiment of the invention, the evaluation control means evaluates, as metabolism of the living body, oxygen saturation of hemoglobin, the quantity of hemoglobin and a degree of oxidation-reduction of Cytaa3. Then, the evaluated metabolism in the body is displayed by display means or recorded by recording means.

The foregoing and other objects, features, aspects and advantages of the present invention will become more apparent from the following detailed description of the present invention when taken in conjuntion with the accompanying drawings.

BRIEF DESCRIPTION OF THE DRAWINGS

FIG. 1 is a diagram showing a principle of the present invention.

FIG. 2 is a diagram showing an example of ultrashort light pulses applied to he CT computed tomograph shown in FIG. 1.

FIG. 3 is a waveform diagram showing a reference light pulse, a transmitted light pulse and a second harmonic of those pulses.

FIG. 4 is a waveform diagram for explaining measurement of a curve $S(\tau)$ with respect to delay time of the second harmonic.

FIG. 5 is a waveform diagram for explaining operation for evaluating $S(\tau)$ by the photon counter shown in FIG. 1.

DESCRIPTION OF THE PREFERRED EMBODIMENTS

Figure 6:
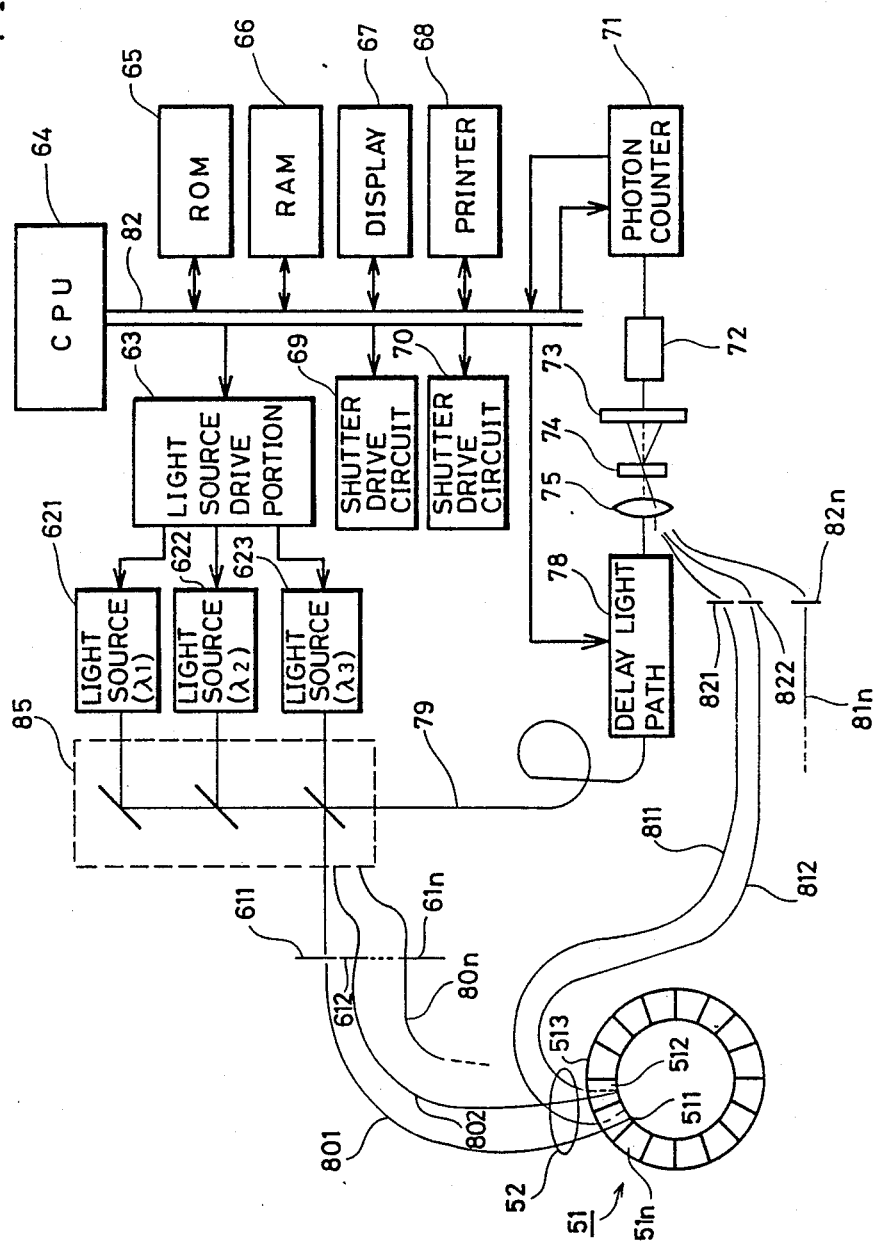
FIG. 6 is a schematic block diagram of an embodiment of the present invention.

FIG. 1 is a diagram for explaining the principle of the present invention; FIG. 2 is a diagram showing an example of ultrashort light pulses applied to the CT computed tomograph shown in FIG. 1; FIG. 3 is a waveform diagram showing a reference light pulse, a transmitted light pulse and a second harmonic of those pulses; and FIG. 4 is a waveform diagram for explaining measurement of a curve $S(\tau)$ with respect to delay time of the second harmonic, where $\tau$ represents the delay time.

First, referring to FIGS. 1 to 4, the principle of the present invention will be described. In this invention, high-repetitive ultrashort light pulses are utilized. Such high-repetitive ultrashort light pulses are obtained in the following manner. By using a semiconductor laser, for example, light pulses of a full-width at half maximum of several tens to several psec (psec$=10^{-12}$ sec) are obtained with a drive current modulation of repetitive modulation frequency 1 GHz. For example, as to the ultrashort light pulses shown in FIG. 2, the interval of light pulses is $10^{-9}$ sec and $10^9$ pulses are generated for one second. Such light pulses can be obtained not only by the semiconductor laser but also by a pigment laser or the like.

Those ultrashort light pulses are branched to reference light pulses advancing straight through a half mirror 11 and sample light pulses advancing in the direction perpendicular thereto. The sample light pulse are applied to a living body 13 to be examined, by means of a mirror 12. The light pulses transmitted through the living body 13 are reflected on mirrors 14 and 15 and introduced into a lens 16. In the following, the sample light pulses are referred to as a transmitted light pulses.

On the other hand, the reference light pulses are reflected on a mirror 19 and introduced into a delay light path 21. Then, those reference light pulses are reflected on a mirror 20 and introduced into the lens 16 in the same manner as in the transmitted light pulses. The delay light path 21 may be a combination of two mirrors as shown in FIG. 1 or it may be a prism or a corner cube. The function of the delay light path 21 will be described afterwards. The lens 16 converges the transmitted light pulses and the reference light pulse and inputs the converged pulses into a non-linear optical crystal 17.

The reference light pulses and the transmitted light pulses before those pulses are inputted to the non-linear optical crystal 17 have waveforms as as shown in FIG. 3. More specifically, the reference light pulses have a little lower power than that of the ultrashort light pulses shown in FIG. 2 but have the same pulse duration. On the other hand, the transmitted light pulses have power considerably lowered when they are transmitted through the living body 13, and as described previously in connection with FIG. 12, light pulses transmitted through the other light paths 10b and 10c than the straight advancing light path 10a are detected and accordingly the pulse duration thereof cannot be maintained equal to that of ultrashort light pulses shown in FIG. 2, causing a trailing form.

Figure 12:
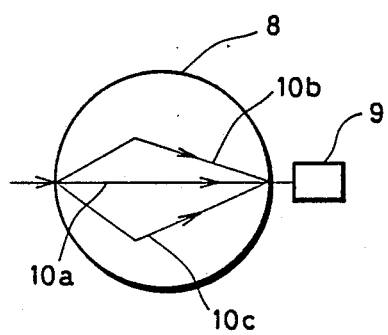
FIGS. 12 and 13 are diagrams showing light paths detected in the conventional measuring apparatus.
Figure 13:
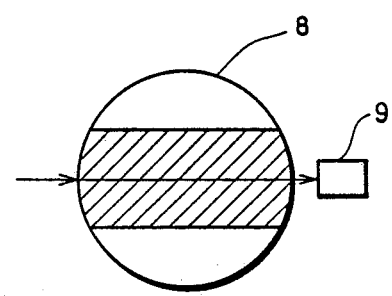

However, it can be confirmed that the rise of each transmitted light pulse represents only the component of light transmitted through the straight advancing light path 10a shown in FIG. 12. This is because the straight advancing light path 10a has the shortest distance among the light paths in the living body 13 and the light through the light path 10a attains the detector 9 the fastest. Thus, by utilizing the pulses rising the fastest such as ultrashort light pulses, only the straight advancing component can be selected and detected.

In order to detect the straight advancing component, the non-linear optical crystal 17 is used. This crystal 17 is a crystal such as LiIO$_3$ or KDP and it generates second harmonic when the reference light pulses and the transmitted light pulses are inputted thereto. The power S of the second harmonic is represented as a function of delay time $\tau$ corresponding to the distance of the delay light path 21 in FIG. 1 and assuming that the reference light pulses ar represented as Ir and that the transmitted light pulses are represented as Is, this power is expressed as follows:

$$S(\tau) \sim \int (Is(t)Ir(t-\tau)dt \text{ tm (1)}$$

Accordingly, $S(\tau)$ is proportional to a value of integration of the product of Is(t) and Ir(t−$\tau$). It is important in this case that even if the transmitted light pulses are considerably attenuated through the living body 13 (in reality, attenuated to $10^{-9}$ of the incident light power through the head of a rat as a result of measurement) and become very weak light, the power S of the second harmonic is the value of integration of the product of the transmitted pulses and the reference light pulses and accordingly the power S of the second harmonic can be detected since the reference light pulses have a large intensity.

The character $\tau$ in the above mentioned expression (1) is delay time corresponding to the distance of the delay light path 21 shown in FIG. 1, as described previously. More specifically, this delay time is time obtained by dividing, by a light speed, a difference of the light paths of the reference light pulses and the transmitted light pulses from he half mirror 11 to the crystal 17. This $\tau$ becomes 0 when the reference light pulses and the transmitted to light pulses reach the crystal 17 simultaneously as shown in FIG. 4 and by changing the delay optical path 21, the reference pulses are delayed with respect to the sample light pulses. More specifically, S is the function of $\tau$ and by changing the delay optical path 21, it is possible to observe the waveform as shown in (c) of FIG. 3. Further, since the rise of the sample light pulse represents a straight advancing component when $\tau=0$, the value of S(0) corresponds to a signal of only the straight advancing component and if this signal is detected, the diffused light components 10b and 10c through the living body as shown in FIG. 12 can be removed and only the straight advancing light component 10a can be detected.

The second harmonic outputted from the crystal 17 is emitted along a medium line of the incident angles of reference light pulses and the transmitted light pulses. The wavelength of the second harmonic is ½ of the wavelength of the ultrashort light pulses shown in FIG. 2. The second harmonic is applied to a photomultiplier 22 through a filter 18. The filter 18 permits only the wavelength of the second harmonic to pass therethrough and accordingly the photomultiplier detects only the component of the second harmonic and outputs photons.

FIG. 5 is a waveform diagram for explaining operation for obtaining $S(\tau)$ by using the photon counter shown in FIG. 1.

Referring to FIG. 5, the operation of the photon counter shown in FIG. 1 will be described. The photon counter 23 performs operations as shown in FIG. 5 to obtain a stable output and to detect $S(\tau)$. More specifically, the photon counter 23 first sets the delay optical path 21 to a predetermined position and carries out operation as shown in (b) of FIG. 5 to detect $S(\tau)$. Thus, the photon counter 23 sets the delay optical path 21 to the predetermined position and counts photons outputted from the photomultiplier 22 at intervals of counting of photons as shown in (b) of FIG. 5. In this case, a photon is counted while five ultrashort light pulses pass through the living body 13 as shown in (a) of FIG. 5. The number of light pulses to be set for each interval depends on the sensitivity of detection of $S(\tau)$ and the larger is the number, the better is the sensitivity.

The process of counting of photons in this case is as shown in (c) of FIG. 5. When a photon counting output is sampled by a sample-and-hold signal as shown in (d) of FIG. 5, a sampled output as shown in (e) of FIG. 5 is obtained. This output corresponds to the count of photons obtained in each photon counting interval. This output is shown by expanding the time base thereof in (f) of FIG. 5, in which an average of five outputs of sampling and holding is $S(\tau)$ in the case of a certain value of $\tau$ to detect a stable value of $S(\tau)$. Needless to say, the number of outputs for averaging is not limited to five and it is defined by stability and sensitivity of the apparatus.

Next, by changing the delay light path 21 of FIG. 1 to change the delay time of the reference light pulses, the value of $S(\tau)$ is obtained in the same manner and an output as shown in (g) of FIG. 5 is obtained. This value of $S_0$ is detected as the straight advancing light component. Although it seems that such processing requires much time, evaluation is carried out in the following manner. Since high-repetitive ultrashort light pulses are used, if those light pulses are light pulses of 1 GHz, 10 psec, for example, the value $S(\tau)$ for a certain value of $\tau$ is obtained in this case as follows:

$$10^{-9} \sec \times 5 \times 5 = 2.5 \times 10^{-8} \sec = 25 \text{ nsec}$$

If the value of S(τ) is obtained with 50 plots, it is obtained by the following equation:

$$50 \times 25 \text{ nsec} = 1.25 \text{ } \mu\text{sec}$$

Theoretically, the detection can be made at this speed, however, in reality, it takes time of about 1 msec since the detection is limited by a counting rate of the photomultiplier 22 for photon counting or a band of a preamplifier subsequent thereto or it takes time for setting the delay optical path 21 mechanically.

Figure 7:
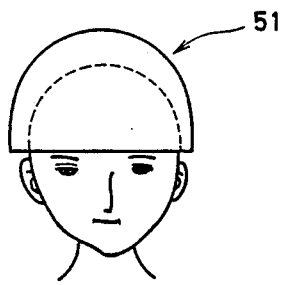
FIG. 7 is an illustration showing a state in which a scanner is attached to the head of a human.
Figure 8:
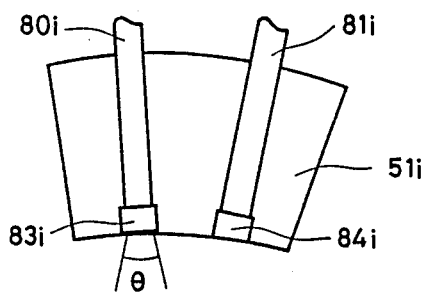
FIG. 8 is a main part sectional view of the scanner.
Figure 9:
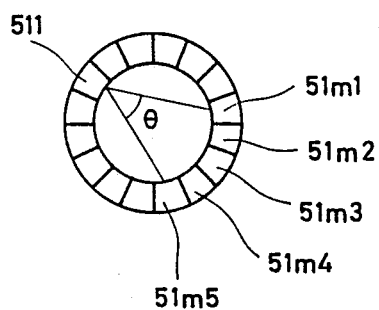
FIG. 9 is a diagram for explaining sample light pulses applied in the scanner.

FIG. 6 is a block diagram showing an embodiment of the present invention; FIG. 7 is an illustration showing a state in which the head of person to be examined is covered with a scanner; FIG. 8 is a sectional view of the scanner; and FIG. 9 is a diagram showing irradiation of light from the scanner.

Referring to FIGS. 6 to 9, construction of the embodiment will be described. A CPU 64 is connected with a ROM 65, a RAM 66, a display 67, a printer 68, a light source drive portion 63 and shutter drive circuits 69 and 70 through a data bus 82. The CPU 64, the ROM 65, the RAM 66, the display 67, the printer 68 and the light source drive portion 63 are the same as shown in FIG. 1. The light source drive portion 63 is connected with light sources 621 to 623 for generating ultrashort light pulses of wavelengths λ1 to λ3 and the ultrashort light pulses generated from the light sources 621 to 623 are applied to a light branching portion 85.

The light branching portion 85 is connected with an optical fiber as a reference light path 79 and also connected with optical fibers as sample light transmitted paths 801 to 80n for guiding a plurality of sample light pulses. Shutters 611 to 61n are provided at intermediate points of those sample light transits paths 801 to 80n. When any of those shutters 611 to 61n is opened, sample light pulses are guided into he corresponding sample light transmitting path. Top ends of the sample light transmitting light paths 801 to 80n are connected to the scanner 51.

The scanner 51 covers the head of the person to be examined as shown in FIG. 7 for example. It is formed in the shape of a ring and it includes ncells 511 to 51n provided at predetermined intervals along its inner surface. The top ends of the sample light transmitting paths 80i (i=1 to n) are connected to the respective cells 511 to 551n as shown in FIG. 8 and a converging lens 83i is provided at each top end. The sample light pulses are collected by those converging lens 83i so that the sample light pulses are applied to the organ of the head of the person to be examined with a predetermined opening angle ¼.

Respective ends of sample light receiving paths 811 to 81n are provided opposite to the organ, in the respective cells 511 to 51n and a collimator lens 84i is attached to each of the ends. The sample light pulses transmitted through the living body are received by those collimator lenses 84i and they are guided into a converging lens 75 through the sample light receiving paths 811 to 81n. Shutters 821 to 82n are provided at intermediate points of the sample light receiving paths 811 to 81n.

The reference light pulses branched by the branching portion 85 are guided into the converging lens 75 from the reference light path 79 through the delay optical path 78. The converging lens 75 converges the reference light pulses and the sample light pulses and applies the converged pulses to the non-linear optical crystal 74. The non-linear optical crystal 74 generates a second harmonic according to the sample light pulses and the reference light pulses and this second harmonic is applied to the photomultiplier 72 through the filter 73. The output of the photomultiplier 72 is supplied to the photon counter 71. The photon counter 71 is the same as the photon counter 23 shown in FIG. 1.

The shutters 611 to 61n provided in the sample light transmitting paths 801 to 80n are driven by the shutter drive circuit 69 and the shutters 821 to 82n provided in the sample light receiving paths 811 to 81n are driven by the shutter drive circuit 70.

Figure 10:
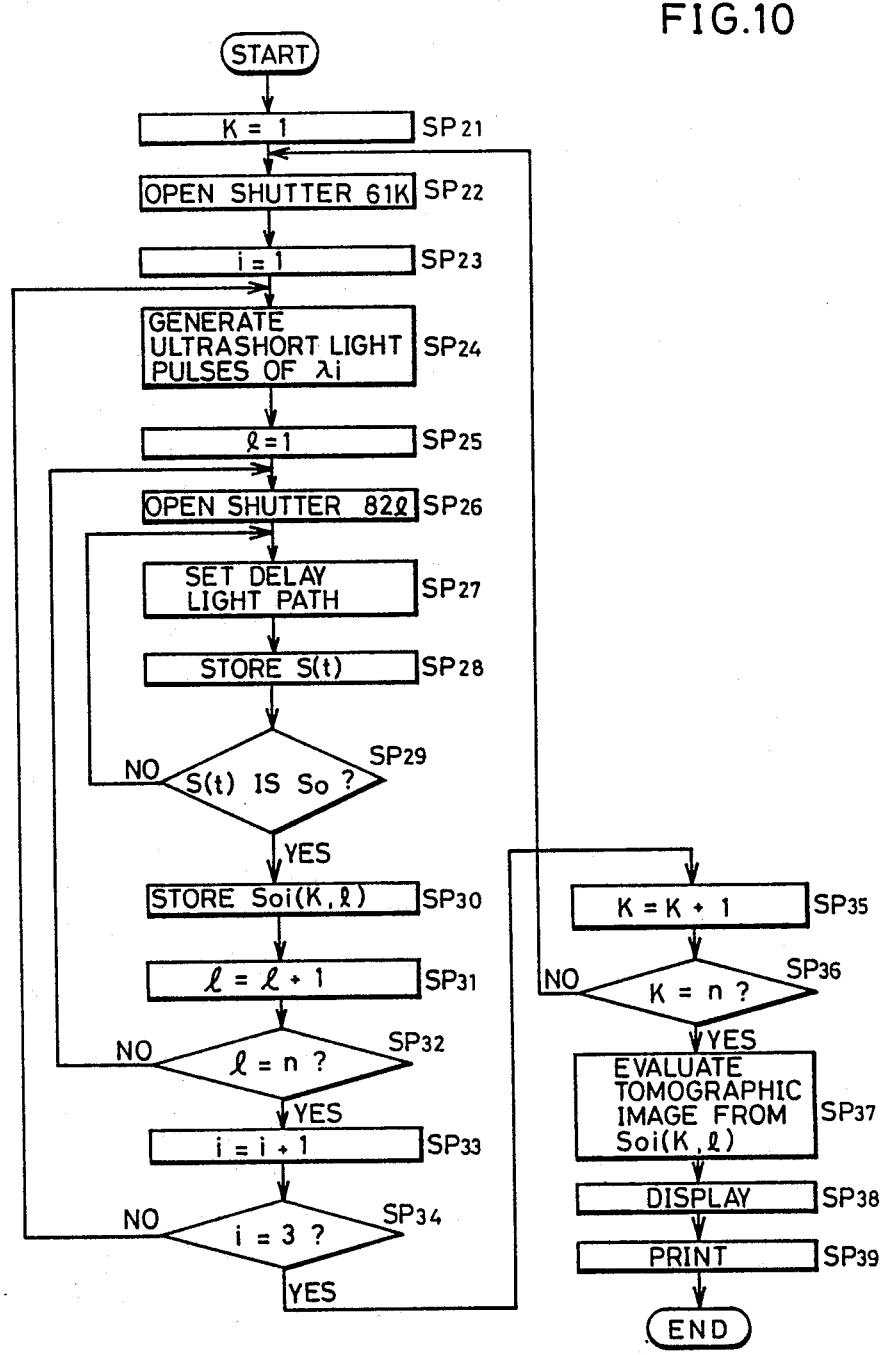
FIG. 10 is a flow chart for explaining specified operation of an embodiment of the invention.
Figure 11:
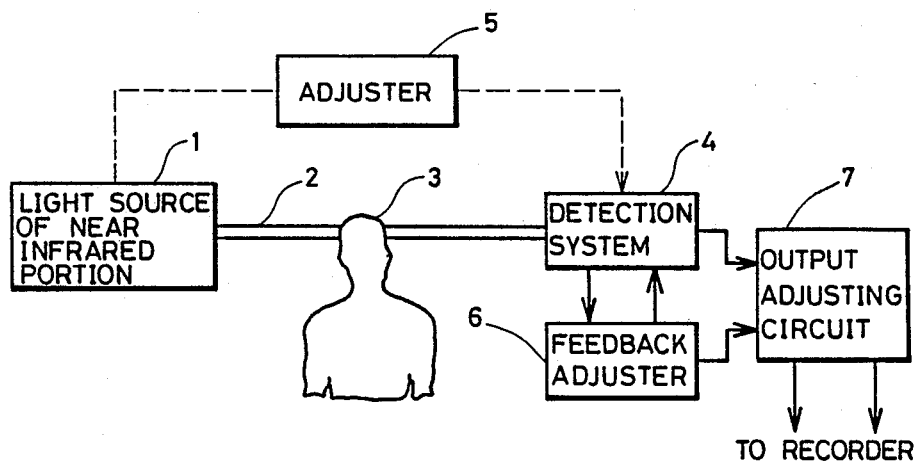
FIG. 11 is a diagram showing a construction of a conventional apparatus for measuring metabolism in an organ of a human body.

FIG. 10 is a flow chart for explaining specified operation of the embodiment of the invention.

Referring to FIGS. 6 to 10, the operation of this embodiment will be described. First, the CPU64 sets k=1 in step SP21. This k is a constant for designating any of the shutters 611 to 61n provided in the sample light transmitting paths 801 to 80n. When the CPU64 sets the constant k=1, the shutter drive circuit 69 opens the shutter 611 in step SP22.

Then, the CPU64 sets i=1 in step SP23. This i is a constant for designating generation of ultrashort light pulses of the wavelength λ1. When the CPU64 sets the constant i=1, the light source drive portion 63 generates ultrashort light pulses of the wavelength λ1 from the light source 621 in step SP24. Consequently, the ultrashort light pulses of the wavelength λ1 generated from the light source 621 are branched to the sample light transmitting path 801 and the reference light path 79 by the light branching portion 85 and transmitted to the scanner 51 through the shutter 611.

In the scanner 51, the sample light is applied from the cell 511 to the organ with the predetermined opening angle θ as shown in FIG. 9. The sample light pulses transmitted through the organ are received by the cell 51m1 for example.

On the other hand, the CPU64 set a constant 1=1 in step SP25. This constant 1 is a constant for designating opening of any of the shutters 821 to 82n provided in the light receiving paths 811 to 81n. The shutter drive circuit 70 opens the corresponding shutter in step SP26 when the CPU64 sets the constant 1=1. In consequence, the sample light pulses received by the cell 51m1 for example in the scanner 51 are converged by the lens 75 through the corresponding sample light receiving path.

At this time, the CPU64 sets a delay time of reference light pulses through the delay optical path 78 in step SP27. More specifically, the CPU64 sets the delay time so that the time required of the sample light pulses to attain the lens 75 through the sample light transmitting path, the organ and tee sample light receiving path is equal to the time required for the reference light pulses to attain the lens 75 through the reference light path 79.

Further, the reference light pulses and the sample light pulses are converged by the lens 75 so as to be applied to the optical crystal 74. Then, a second harmonic is generated by the optical crystal 74 and the second harmonic is inputted to the photomultiplier 72 through the filter 73. The photon counter 71 counts photons based on the output of the photomultiplier 72 and supplies the count output to the CPU64. The CPU64 ealuates S(τ) based on the output of the photon counter 71 in the same manner as described above, in step SP28 and stores the result of the evaluation in the RAM66. Further, the CPU64 determines in step SP29 whether S(τ) becomes $S_0$ or not. If it is not $S_0$, the above mentioned steps SP27 to SP29 are repeated.

When the CPU64 determines that $S(\tau)$ becomes $S_0$, it stores $S_{01}(1, m1)$ in the RAM66 in step SP30. In addition, the CPU64 increments the constant 1 by one in step SP31. Thus, the sample light pulses are received by the cell 51m2 adjacent to the cell 51m1 of the scanner 51. The CPU64 determines in step SP32 whether the constant 1 is n or not. This is for the purpose of determining whether the respective shutters of the sample light receiving paths 811 to 81n have been successively opened or not. If the constant 1 is not n, the CPU64 opens the shutter corresponding to the cell 51m2 of the scanner 51 in step SP26. By repeating this operation, the sample light pulses of the wavelength $\lambda 1$ are applied to the organ and the sample light pulses received by the respective cells of the scanner 51 are successively guided into the optical crystal 74, whereby the photon counter 71 stores $S_{01}(1, m2)$, $S_{01}(1, m3)$ ... $S_{01}(1, n)$.

Then, in order to generate ultrashort light pulses of the wavelength $\lambda 2$, the CPU64 increments the constant i by one in step SP33 and determines in step SP34 whether the constant i becomes 3 or not. If the constant i is not 3, the ultrashort light pulses of the wavelength $\lambda 2$ are generated from the light source 622 n step SP24. Then, in the same manner as described inaabove, the steps SP25 to SP33 are repeated so that $S_{02}(1, m1)$, $S_{02}(1, m2)$ ... $S_{02}(1, n)$ are stored.

The CPU64 repeats the steps SP24 to SP34 for the wavelength $\lambda 2$ and further increments the constant i by one and then repeats the steps SP24 to SP34 for the wavelength $\lambda 3$. When it is determined in step SP34 that the constant i is 3, the CPU64 increments the constant k by one in step SP35 to open the shutter 612 provided in the sample light transmitting path 802. The CPU64 determines in step SP36 whether the constant k is equal to n or not. This is for the purpose of determining whether the shutters 611 to 61n are successively opened or not. If the constant k is not n, the CPU64 repeats the steps SP22 to SP34 and stores $S_{0i}(k, l)$ (i=1, 2 or 3, k, l=1 to n) in the RAM66 based on the respective ultrashort light pulses of the wavelength $\lambda 1$ to $\lambda 3$. Then, when it is determined in step SP36 that the constant k is n, the CPU64 processes data according to an algorithm for evaluating a hemoglobin quantity, an oxygen saturation and Cytaa3 in blood to obtain the quantity of hemoglobin, the oxygen saturation and a tomographic image of Cytaa3 in the brain. Thus, in step SP38, the CPU64 displays those results on the display 67 and prints the results by means of the printer 68 in step SP39.

Although in the above described embodiment, the head of a human body is to be examined, the body to be examined is not limited thereto. The form of the scanner 51 may be changed suitably according to the body to be examined, whereby the oxygen saturation and other data of the body can be measured.

In addition, the parameters for measurement are not limited to the oxygen saturation in the brain and the like. Other parameters may be used insofar as they concern information of a living body obtained by measuring absorbance of light.

Further, in the embodiment shown in FIG. 6, light pulses of the three wavelengths $\lambda 1$, $\lambda 2$ and $\lambda 3$ are generated. However, light pulses of more than three wavelengths may be generated. Needless to say, those wavelengths $\lambda 1$, $\lambda 2$, and $\lambda 3$ have a particularly good transmittivity of a living body in the range from 700 nm to 1300 nm and enable detection of metabolism such as hemoglobin and Cytaa3.

As described in the foregoing, according to the embodiment of the invention, the sample light pulses of the different wavelengths are applied to the living body from the scanner and the sample light pulses transmitted through the body and reference light pulses are collected and introduced into the crystal so that the second harmonic is generated. Then, based on the second harmonic, photons are counted and an average value of photons is obtained. Consequently, diffused components of the transmitted light through the body can be removed and only the straight advancing component on the incident optical axis can be detected. Thus, it is possible to monitor a tomographic image indicating the tissue metabolism on a specified axis in the body. In addition, since the high-repetitive ultrashort light pulses are utilized, the detection sensitivity of the quantity of transmitted light can be considerably improved and since the sensitivity can be changed simply, the operation efficiency can be improved.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A CT computed tomograph for measuring metabolism of a living body of a human or an animal to be examined, comprising:

light sources (621, 622, 623) for generating high-repetitive ultrashort light pulses of a plurality of wavelengths, light branching means (85) for branching said ultrashort light pulses generated from said light sources to reference light pulses and sample light pulses, a reference light path (79) for introducing the reference light pulses branched by said light branching means, a scanner (51) formed in the shape of a ring surrounding the living body of said human or animal to be examined, and including a plurality of cells sectioned at predetermined intervals along its inner circumferential surface, a plurality of sample light transmitting paths (801, 80n) having respective ends in the cells of said scanner, opposite to said living body, and having respective other ends to which the sample light pulses branched by said light branching means are applied, sample light receiving paths (811 to 81n) having respective ends in the cells of said scanner opposite to said living body and respective other end from which the sample light pulses transmitted through said living body are introduced, delay means for delaying the light pulses in any one of said reference light path, said sample light transmitting paths and said sample light receiving paths by a predetermined time, converging means (75) for converging the reference light pulses introduced through said reference light path and the sample light pulses transmitted through said sample light receiving paths, a crystal (74) for generating a second harmonic based on the light pulses converged by said converging means, second harmonic detecting means (72) for detecting the second harmonic generated from said crystal, and evaluation control means (64) for applying, to said living body in said scanner, the ultrashort light pulses of the ith wavelength from the sample light transmitting path corresponding to the kth cell, converging the sample light pulses received by the sample light receiving path corresponding to the lth cell and said reference light pulses by said converging means, counting photons outputted from said second harmonic detecting means based on the converged light pulses, obtaining an average value by averaging a predetermined number of count values, changing a delay amount of either the sample light pulses or the reference light pulses by said delay means based on said average value, storing a photon average value $S_{0i}(k, l)$ (where $k, l = 1, 2, \ldots n$ and $i = 1, 2, \ldots m$) of the count value of photons of said second harmonic when the delay amount of the reference light pulses and the sample light pulses is a predetermined value, based on delay time and an average value in said delay time, and evaluating a tomographic image of the metabolism in said living body based on said photon average value $S_{0i}(k, l)$.

2. A CT computed tomograph in accordance with claim 1, further comprising
first shutter means (611 to 61n) provided corresponding to the respective sample light transmitting paths, for shutting off the sample light pulses supplied from said light branching means,
said evaluating control means including first shutter drive means (69) for opening any one of said first shutter means.

3. A CT computed tomograph in accordance with claim 1, further comprising
second shutter means (821 to 82n) provided corresponding to the respective sample light receiving paths, for shutting off the sample light pulses transmitted through said living body,
said evaluation control means including second shutter drive means (70) for opening any one of said second shutter means.

4. A CT computed tomograph in accordance with claim 1, further comprising
a filter (73) provided between said crystal and said second harmonic detecting means, for permitting only the second harmonic generated from said crystal to pass therethrough.

5. A CT computed tomograph in accordance with claim 1, wherein
said evaluation control means evaluates, as the metabolism of said living body, an oxygen saturation of hemoglobin, a quantity of hemoglobin and an oxidation-reduction degree of Cytaa3 from said photon average value $S0i(k, l)$.

6. A CT computed tomograph in accordance with claim 5, further comprising
display means (67) for displaying the metabolism of said living body evaluated by said evaluation control means.

7. A CT computed tomograph in accordance with claim 5, further comprising
recording means (68) for recording the metabolism of said living body evaluated by said evaluation control means.

* * * * *

UNITED STATES PATENT AND TRADEMARK OFFICE
CERTIFICATE OF CORRECTION

PATENT NO. : 4,910,404

DATED : March 20, 1990

INVENTOR(S) : Yoshio Cho et al.

It is certified that error appears in the above-identified patent and that said Letters Patent is hereby corrected as shown below:

In the Abstract [57], line 20, before "is stored" insert --.--.

Column 1, line 7, replace "in an" by --in a--;

Column 1, line 51, replace "two-dimentional" by --two-dimensional--;

Column 2, line 51, replace "is provided to oppose" by --is positioned opposite--;

Column 7, line 5, replace "takes time of" by --takes--;

Column 8, line 11, replace "for explaining" by --for explaining the--;

Column 8, line 36, replace "set a" by --sets a--.

In the Claims:

Claim 1, Column 10, line 52, replace "other end" by --other ends--.

UNITED STATES PATENT AND TRADEMARK OFFICE
CERTIFICATE OF CORRECTION

PATENT NO. : 4,910,404

DATED : March 20, 1990

INVENTOR(S) : Yoshio Cho et al.

It is certified that error appears in the above-identified patent and that said Letters Patent is hereby corrected as shown below:

Claim 1, Column 10, line 52, replace "other end" by --other ends--.

Signed and Sealed this

Twenty-eighth Day of May, 1991

Attest:

HARRY F. MANBECK, JR.

*Attesting Officer*    *Commissioner of Patents and Trademarks*